US008286671B1

(12) United States Patent  
Strangis

(10) Patent No.: US 8,286,671 B1
(45) Date of Patent: Oct. 16, 2012

(54) AUTOMATED SYRINGE FILLER AND LOADING APPARATUS

(76) Inventor: Saverio Roberto Strangis, Pearland, TX (US)

( * ) Notice: Subject to any disclaimer, the term of this patent is extended or adjusted under 35 U.S.C. 154(b) by 22 days.

(21) Appl. No.: 13/069,745

(22) Filed: Mar. 23, 2011

(51) Int. Cl.
  B65B 3/04 (2006.01)
(52) U.S. Cl. ............... 141/9; 141/27; 141/104; 141/144; 141/145; 141/270; 141/281; 604/416
(58) Field of Classification Search ............ 141/1, 9, 141/18, 26, 27, 104, 105, 144–146, 270, 141/281; 600/5; 604/414, 416
See application file for complete search history.

(56) References Cited

U.S. PATENT DOCUMENTS

| | | |
|---|---|---|
| 2,571,302 A | 10/1951 | Smith |
| 3,662,517 A | 5/1972 | Taschar et al. |
| 3,734,147 A | 5/1973 | Borutta et al. |
| 3,833,030 A | 9/1974 | Waldbauer, Jr. et al. |
| 3,853,158 A | 12/1974 | Whitty |
| 3,880,211 A * | 4/1975 | Gess ............................ 141/258 |
| 3,935,883 A | 2/1976 | Stach et al. |
| 4,187,890 A | 2/1980 | Stach et al. |
| 4,196,732 A | 4/1980 | Wardlaw |
| 4,252,159 A | 2/1981 | Maki |
| 4,357,971 A * | 11/1982 | Friedman ...................... 604/218 |
| 4,364,388 A | 12/1982 | Cech |
| 4,401,108 A | 8/1983 | Galkin et al. |
| 4,434,820 A | 3/1984 | Glass |
| 4,489,766 A | 12/1984 | Montada |
| 4,501,306 A | 2/1985 | Chu et al. |
| 4,775,369 A | 10/1988 | Schwartz |
| 4,883,101 A | 11/1989 | Strong |
| 5,039,863 A | 8/1991 | Matsuno et al. |
| 5,078,695 A | 1/1992 | Farrar, Jr. et al. |
| 5,224,937 A | 7/1993 | Van der Heiden et al. |
| 5,288,285 A | 2/1994 | Carter |
| 5,292,318 A | 3/1994 | Haber et al. |
| 5,304,165 A | 4/1994 | Haber et al. |
| 5,329,976 A | 7/1994 | Haber et al. |

(Continued)

FOREIGN PATENT DOCUMENTS

WO    WO2006/124891    11/2006

Primary Examiner — Timothy L Maust
Assistant Examiner — Timothy Kelly
(74) Attorney, Agent, or Firm — David McEwing

(57) ABSTRACT

The disclosure pertains to an automated apparatus for filling capped needle syringes. The syringes are held in a rotatable motor controlled carousel. The carousel turns to place a syringe proximate to a dispenser mechanism. A rotatable plate on top of the dispenser mechanism holds an automated cap extractor/installer and at least one inverted vial having a needle perforatable surface. The rotatable plate can also move up and down relative to the top of the dispenser mechanism. The cap can be removed by the automated cap extractor/installer and the rotatable plate rotated to place the inverted vial over the exposed syringe needle. The rotatable plate can descend so that the needle perforates the surface of the vial. A syringe plunger tool of the dispenser mechanism engages the syringe plunger and pulls it downward. The syringe plunger tool can disengage and return to its original position. The rotatable plate can raise to remove the needle from the vial. The rotatable plate can rotate to place the automated cap extractor/installer over the exposed needle. The automated cap extractor/installer holding the syringe needle cap can descend and the cap reattached to the syringe. The carousel can rotate to present the filled and capped syringe to an automated syringe inverter/extractor component that removes the capped syringe from the carousel and places the syringe in a holder.

15 Claims, 20 Drawing Sheets

U.S. PATENT DOCUMENTS

| | | | |
|---|---|---|---|
| 5,341,854 | A | 8/1994 | Zezulka et al. |
| 5,385,559 | A | 1/1995 | Mannix |
| 5,479,969 | A | 1/1996 | Hardie et al. |
| 5,487,738 | A | 1/1996 | Sciulli |
| 5,620,422 | A | 4/1997 | Halbich |
| 5,911,252 | A | 6/1999 | Cassel |
| 5,927,351 | A | 7/1999 | Zhu et al. |
| 6,189,195 | B1 | 2/2001 | Reilly et al. |
| 6,702,785 | B1 | 3/2004 | Collins |
| 6,813,868 | B2 | 11/2004 | Baldwin et al. |
| 6,877,530 | B2 * | 4/2005 | Osborne et al. ............ 141/27 |
| 6,915,823 | B2 * | 7/2005 | Osborne et al. ............ 141/27 |
| 6,976,349 | B2 | 12/2005 | Baldwin et al. |
| 7,025,098 | B2 | 4/2006 | Osborne |
| 7,025,757 | B2 | 4/2006 | Reilly et al. |
| 7,163,031 | B2 | 1/2007 | Graves et al. |
| 7,207,152 | B2 | 4/2007 | Baldwin |
| 7,240,699 | B2 | 7/2007 | Osborne et al. |
| 7,343,724 | B1 | 3/2008 | Williams et al. |
| 7,398,802 | B2 * | 7/2008 | Baker ..................... 141/27 |
| 7,571,747 | B2 | 8/2009 | Spitz |
| 7,631,475 | B2 | 12/2009 | Baldwin et al. |
| 7,677,275 | B2 | 3/2010 | Witte |
| 7,681,606 | B2 * | 3/2010 | Khan et al. ............. 141/147 |
| 7,703,483 | B2 | 4/2010 | Hartman et al. |
| 7,712,491 | B2 | 5/2010 | Tochon-Danguy et al. |
| 7,750,328 | B2 | 7/2010 | Tartaglia |
| 7,861,750 | B2 | 1/2011 | Py et al. |
| 8,181,677 | B2 * | 5/2012 | Li et al. ................ 141/275 |
| 2001/0018937 | A1 | 9/2001 | Nemoto |
| 2002/0020459 | A1 | 2/2002 | Baldwin et al. |
| 2003/0103839 | A1 | 6/2003 | Osborne et al. |
| 2004/0103951 | A1 | 6/2004 | Osborne et al. |
| 2004/0104243 | A1 | 6/2004 | Osborne et al. |
| 2005/0173021 | A1 | 8/2005 | Muto et al. |
| 2005/0199647 | A1 | 9/2005 | Muto et al. |
| 2005/0203329 | A1 | 9/2005 | Muto et al. |
| 2005/0278066 | A1 | 12/2005 | Graves et al. |
| 2006/0151048 | A1 | 7/2006 | Tochon-Danguy et al. |
| 2006/0201575 | A1 | 9/2006 | Osborne |
| 2007/0161959 | A1 | 7/2007 | Spitz |
| 2008/0004480 | A1 | 1/2008 | Bedeschi |
| 2008/0035234 | A1 | 2/2008 | Khan et al. |
| 2008/0053560 | A1 | 3/2008 | Hartman et al. |
| 2008/0114328 | A1 * | 5/2008 | Doherty et al. ............ 604/414 |
| 2008/0142743 | A1 | 6/2008 | Tartaglia |
| 2008/0166292 | A1 | 7/2008 | Levin et al. |
| 2008/0169044 | A1 | 7/2008 | Osborne et al. |
| 2008/0171999 | A1 | 7/2008 | Baplue et al. |
| 2009/0038709 | A1 | 2/2009 | VanVreeland et al. |
| 2009/0108018 | A1 | 4/2009 | Li et al. |
| 2009/0131862 | A1 | 5/2009 | Buck et al. |
| 2009/0166370 | A1 | 7/2009 | De Turk et al. |
| 2009/0178726 | A1 | 7/2009 | Spitz |
| 2010/0059139 | A1 | 3/2010 | Pond et al. |
| 2010/0059140 | A1 | 3/2010 | Pond et al. |
| 2010/0331600 | A1 | 12/2010 | Bae et al. |
| 2011/0100501 | A1 * | 5/2011 | Mizuno et al. ............ 141/2 |
| 2011/0168293 | A1 * | 7/2011 | Van Vreeland et al. ......... 141/9 |

* cited by examiner

AUTOMATED SYRINGE FILLER AND LOADING APPARATUS

BACKGROUND OF INVENTION

1. Field of Use

The disclosure teaches a method and apparatus for automated filling of syringes. This includes automated filling of syringes with radiopharmaceuticals or other drugs.

2. Prior Art

Semi automated systems for filling syringes have been disclosed in the prior art including machines manufactured by Intellifill iv of FHT Inc., Daytona Beach, Fla. and Radio Syringe Filling by M&O Perry Industries of Corona, Calif.

BRIEF SUMMARY OF DISCLOSURE

The apparatus subject of the disclosure can be used to prepare (fill) syringes containing liquids including pharmaceuticals or radiopharmaceutical without operator participation. The apparatus can also be used to fill vials of solutions or mix solutions within a vial. When the solution is radioactive, the syringe filling operation can be performed in a suitably shielded location for operator safety.

The capping, filling and recapping of the syringe needles is performed automatically away from the operator, therefore eliminating any danger of accidental needle sticks during the filling operation.

The disclosure outlines a series of automated steps performed by the apparatus or components of the apparatus. It will be appreciated that the sequence in which these steps are performed may be varied without departing from the scope of the disclosed invention.

The syringes are filled while in an inverted position with the pharmaceutical, radiopharmaceutical, medication, radioisotopes or other drug or hazardous substance, hereinafter "solution", positioned above the syringe. This allows for gravity vacuum feed of the solution. In an inverted position, the capped syringe needle is pointed up and the syringe plunger is at the bottom. The empty syringes are loaded onto a rotatable carousel or loaded individually into a single syringe adapter/holder. The carousel rotates a predetermined arc placing a syringe adjacent to a dispenser mechanism. The dispenser mechanism contains an automated syringe plunger tool and a rotatable component containing one or more inverted vials of solution and an automated needle cap extractor.

The syringe plunger tool may first engage the syringe plunger. The syringe plunger tool extends from the dispenser mechanism and engages the plunger of the syringe held in the carousel. This can secure the syringe in a stationary position during removal and replacement of the syringe cap and insertion of the needle into an inverted vial. It will be appreciated that the syringe plunger extends from the bottom of the syringe held in the carousel or single syringe adapter/holder.

The needle cap may next be removed from the syringe. The inverted vial rotates above the now exposed syringe needle. A vial of medication is aligned with the needle and the vial descends upon the needle and is perforated by the needle. The tool pulls the plunger down a predetermined distance. This causes a predetermined quantity of solution to be dispensed from the vial into the syringe.

The inverted vial is re-elevated to its original position, the rotatable plate rotates and the syringe cap descends upon the needle.

The carousel again rotates a predetermined arc and places the now filled syringe in front of an automated syringe extractor/inverter component. The syringe inverter component extends and grips the syringe and pulls it horizontally from the carousel. The gripper rotates the syringe about an horizontal axis such that the syringe needle is now pointed down and placed in a holder. The filled syringe can be manually removed from the syringe inverter component or placed in a further automated device. In another embodiment, the syringe is lifted from the carousel.

SUMMARY OF DRAWINGS

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

DETAILED DESCRIPTION

The subject of this disclosure is an automated apparatus for filling syringes. The syringes can be filled with radiopharmaceuticals or other substances. The filling can be performed without handling by human operators or technicians. Radiopharmaceuticals are radioactive pharmaceuticals and can be used in the field of nuclear medicine as tracers in the treatment and diagnosis of many diseases. Radiopharmaceuticals include, but are not limited to, [N13] ammonia, [F-18] sodium fluoride, or [F-18] Fludeoxyglucose ([F-18] FDG).

The process starts with a rotatable carousel 110 having a plurality of slots or holders 111 containing capped empty syringes 211 being placed on a motorized rotating holder (carousel) removeably mounted on a carousel actuator.

Figure 1:
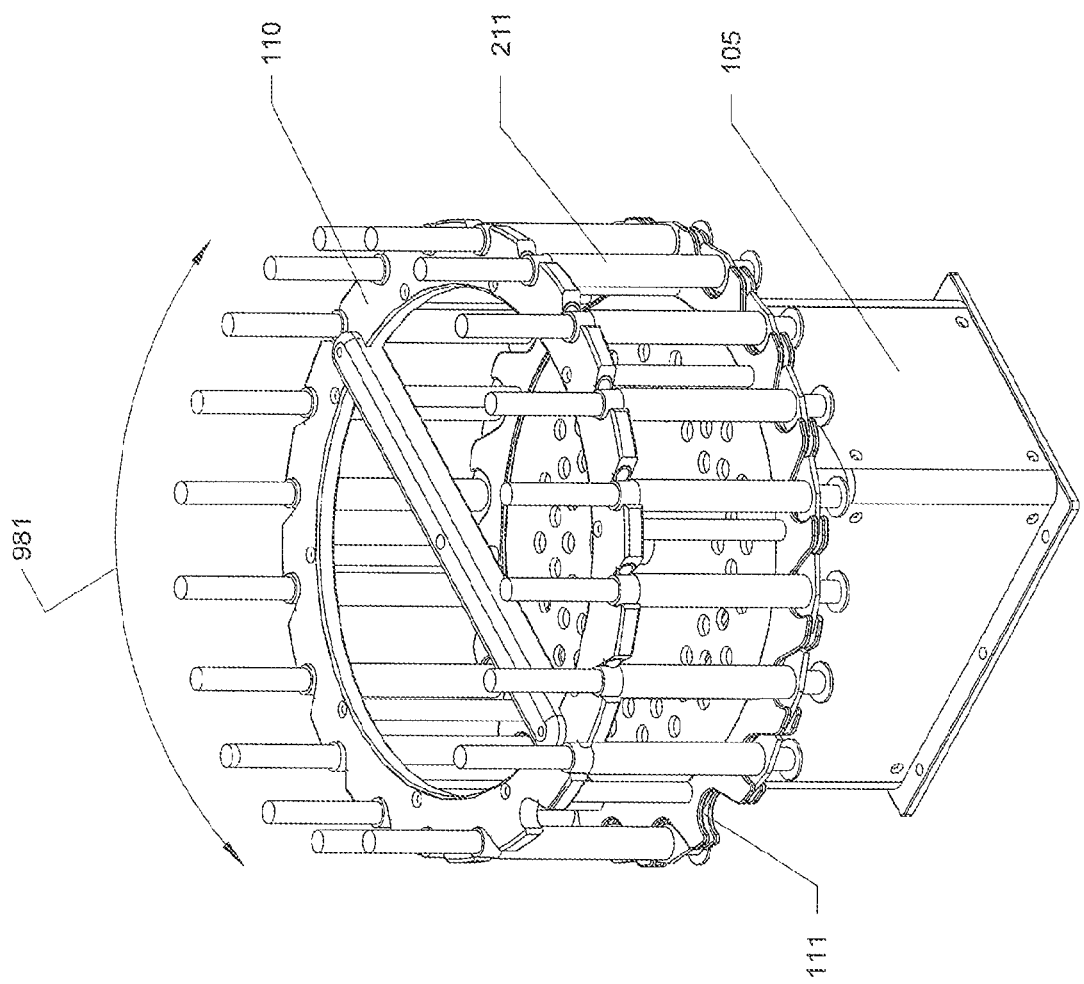
FIG. 1 illustrates the carousel carrying the capped syringes. Also illustrated is the actuator housing rotating the carousel.

In one embodiment, the carousel 110 is placed on the carousel actuator 105 and rotated 45 degrees to attach it to the actuator 105. In another embodiment, the plunger tool or other mechanism actuate the carousel removing pins 193. The pins push the carousel up a few millimeters to break the force of the coupling magnets 192. The carousel may then be easily removed from the carousel actuator. See FIG. 1. The rotational movement can be controlled. The controller for the rotating holder and the other components described below can be performed by a CPU or similar device containing programmable media.

Figure 2:
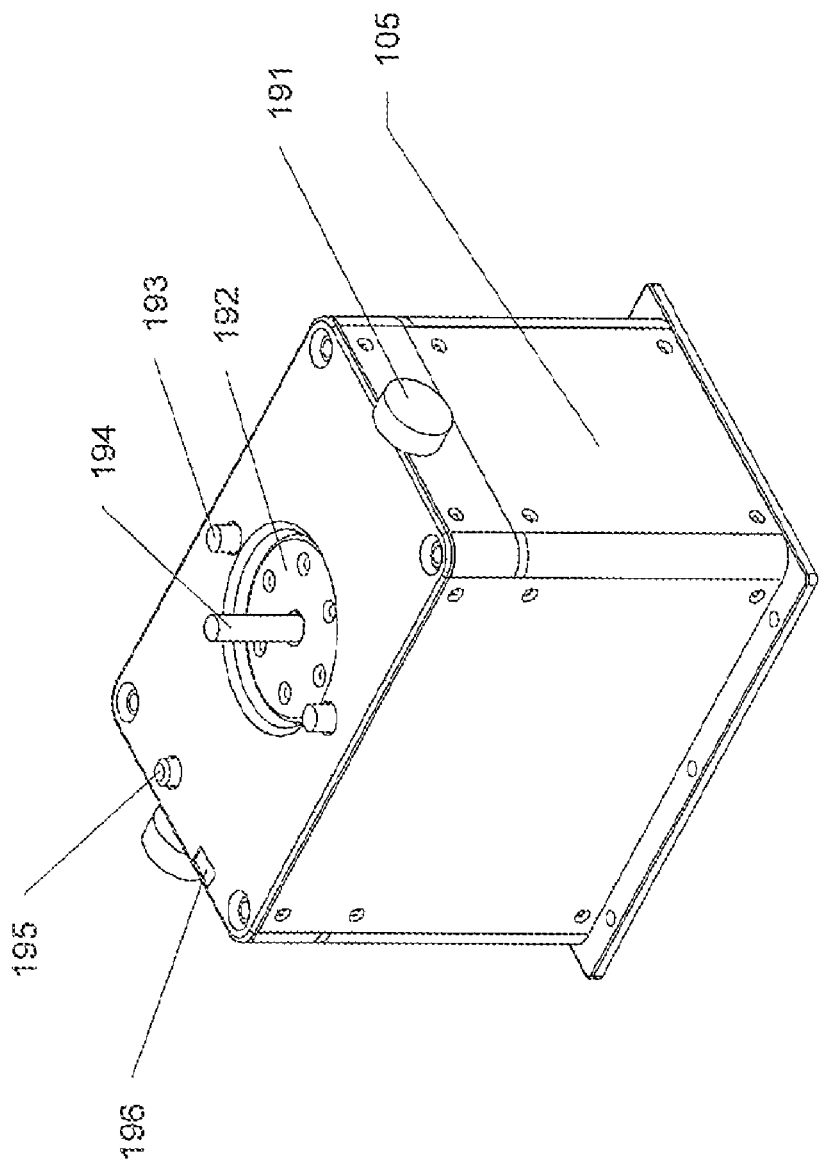
FIG. 2 illustrates the carousel actuator.

Referring to FIG. 2, the carousel actuator 105 is illustrated. Shown are the carousel track rollers 191, carousel presence sensor 196, syringe carousel locking pin 195, coupling mechanism 192, syringe carousel removal pins 193, and rotating shaft 194. In one embodiment, the carousel locking pin 195 serves to lock the carousel in place. When the pin is actuated up, it fits into the carousel holes. This function protects the mechanism when the syringe extractor/inverter extracts the syringe. The syringe carousel removal pins 193 push the carousel up to reduce the force needed to release the coupling mechanism 192, The syringes are placed in the carousel with the capped ends pointed upward and the syringe plungers pushed into the syringe with the plunger ends extending from the bottom of each syringe. Each syringe is held in an individual holder 111 of the carousel. In one embodiment, the syringes are not grasped or held in the individual holder of the carousel. It is possible to lift or pull the syringe horizontally out of the carousel without the release of any mechanism. Each syringe is held vertically in the carousel.

Figure 3:
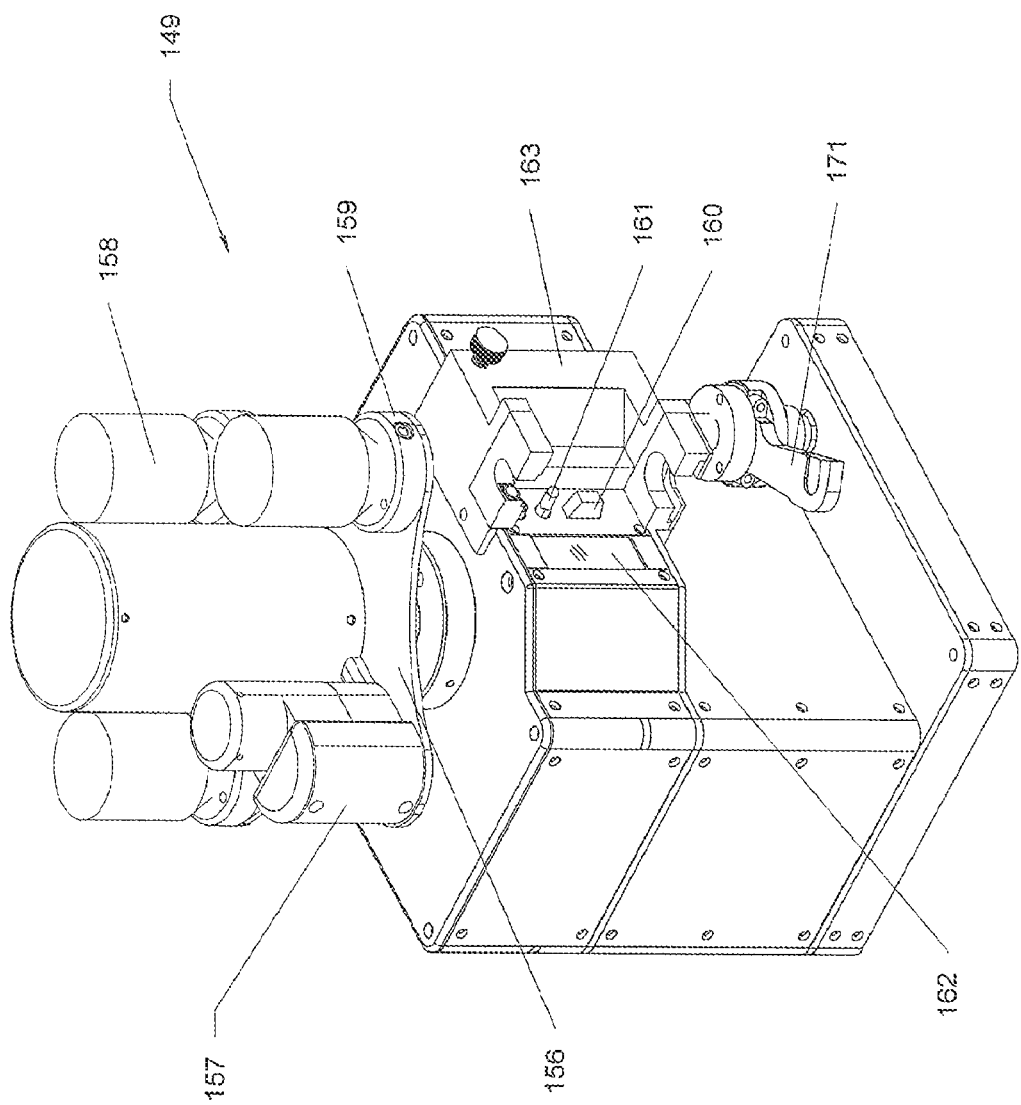
FIG. 3 illustrates the filler mechanism showing 3 vials and the needle cap extractor and placement component. The rotating plate on top of the filler mechanism is also illustrated. Also illustrated is the syringe plunger tool.

The carousel rotates in a controlled fashion. The carousel actuator can be mounted on a common base 148 of the filler (dispenser) mechanism 149. See FIG. 13. This can ensure the proper distance relationship is maintained between the carousel and the filler mechanism and syringe inverter/extractor. Referring to FIG. 3, the carousel is positioned in conjunction with the filler mechanism so that the needle 202 held in the carousel stops under a top rotating plate 156 holding at least one vial of solution 158, e.g., radioisotopes, and an automated needle cap extractor 157. In one embodiment, the movement of the carousel rotation can be controlled by a step motor. In another embodiment, the rotational movement can be controlled by a computer controlled servo-motor. In yet another embodiment, the carousel can be manually rotated. The disclosure includes the ability to stop the rotation of the carousel beneath the automated needle cap extractor or inverted vial. When stopped, a syringe is positioned below the needle cap extractor. When stopped a filled syringe may also be positioned in a carousel slot front of the syringe inverter/extractor component as discussed below.

Figure 7:
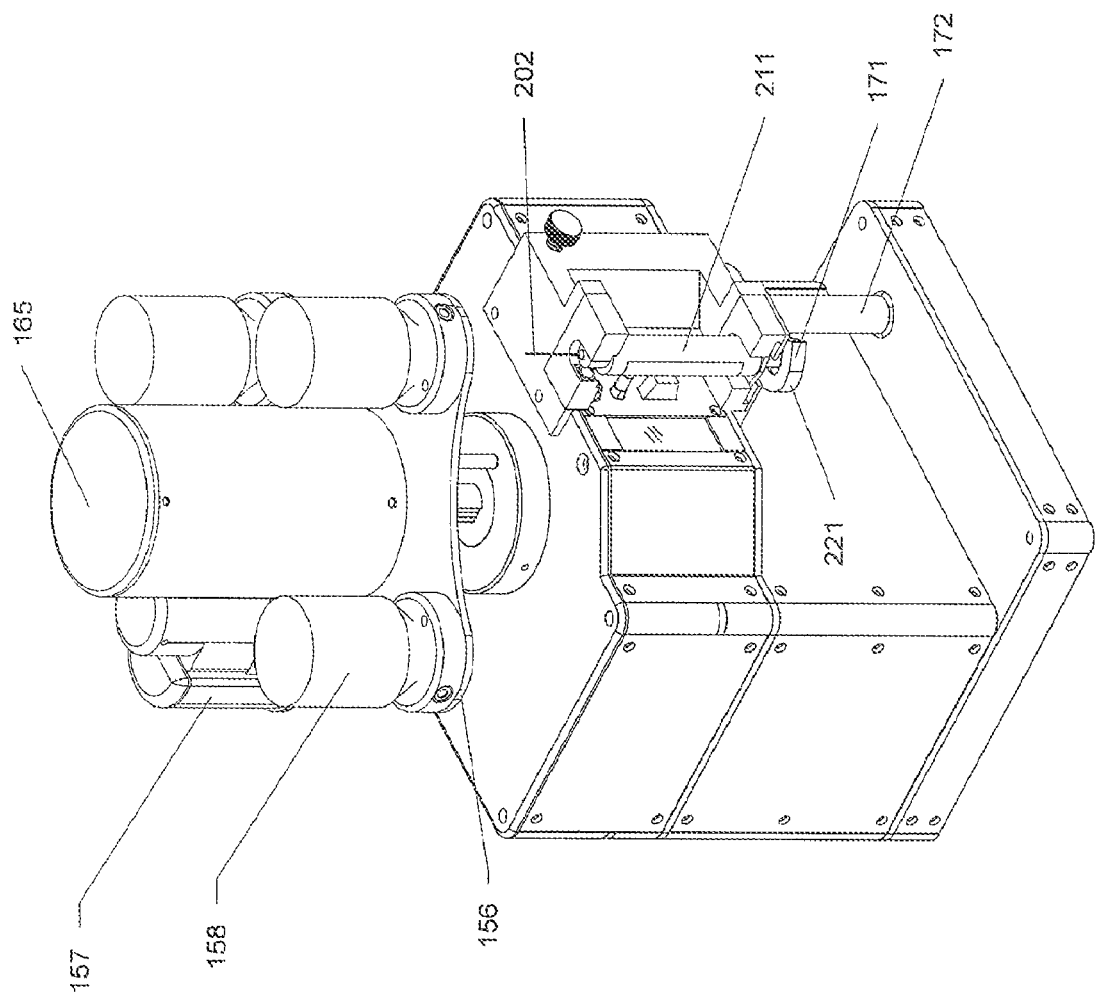
FIG. 7 is a perspective view showing the filler mechanism rotating plate having rotated and positioned an inverted vial above the exposed needle.
Figure 8:
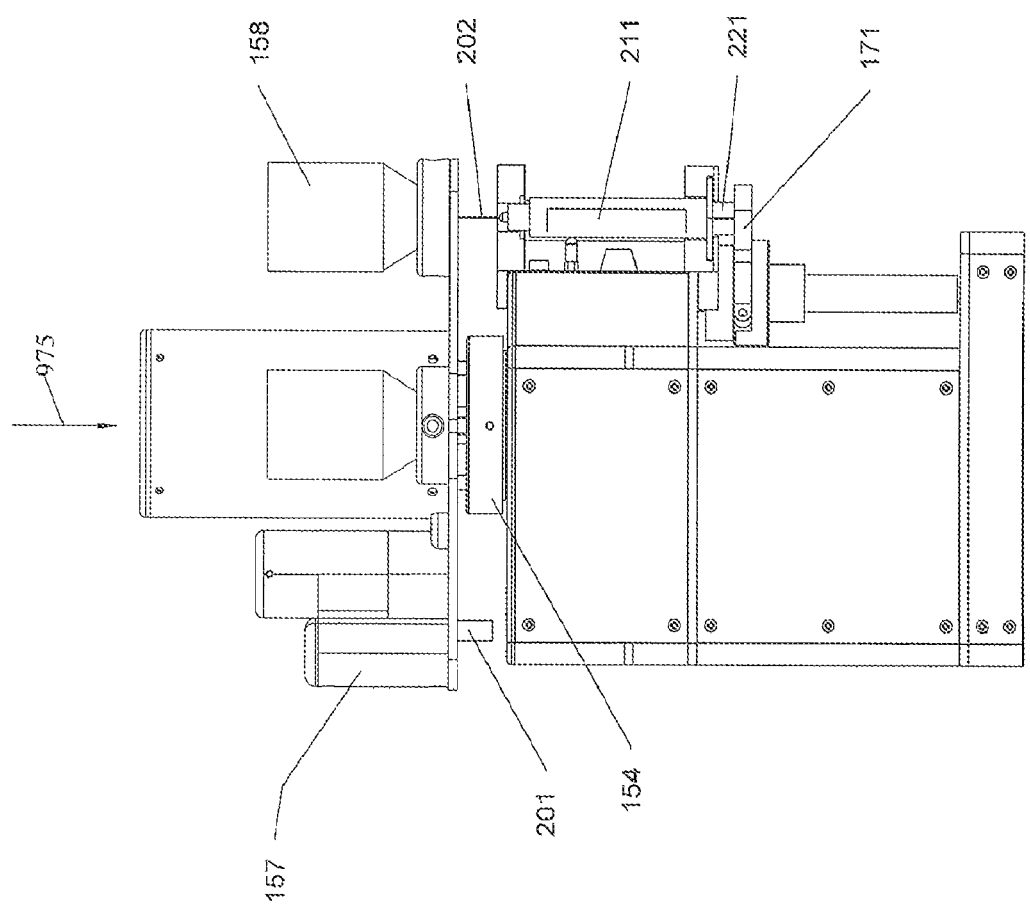
FIG. 8 is a side view of the filler mechanism showing the syringe plunger tool in position to move the syringe plunger downward. Also illustrated is the vial having moved downward onto the exposed syringe needle.

Referencing FIG. 8, at this time, a separate syringe plunger tool 171 may be rotated horizontally forward and engages with the plunger 221 of the inverted syringe. This movement is illustrated by vector arrow 978 in FIG. 13. This engagement occurs at the bottom of the carousel. The syringe plunger tool rotates about component 172. See FIG. 7. It will be appreciated that FIGS. 7 and 8 illustrate the optional single syringe holder mount.

FIG. 3 illustrates the filler mechanism 149 comprised of at least one vial 158, vial holder 159, automated needle cap extractor 157, syringe presence and size sensors 160 and 161 (e.g., 3 ml and 5 ml) and barcode reader window 162. Also illustrated is an optional single syringe holder mount 163. (The optional single syringe holder mount is removed for operation of the carousel with the filler mechanism.) Also disclosed is a syringe 211 and the syringe plunger tool 171. Finally, the top rotating plate 156 is disclosed holding at least one inverted vial 158 and a needle cap extractor 157.

Figure 4:
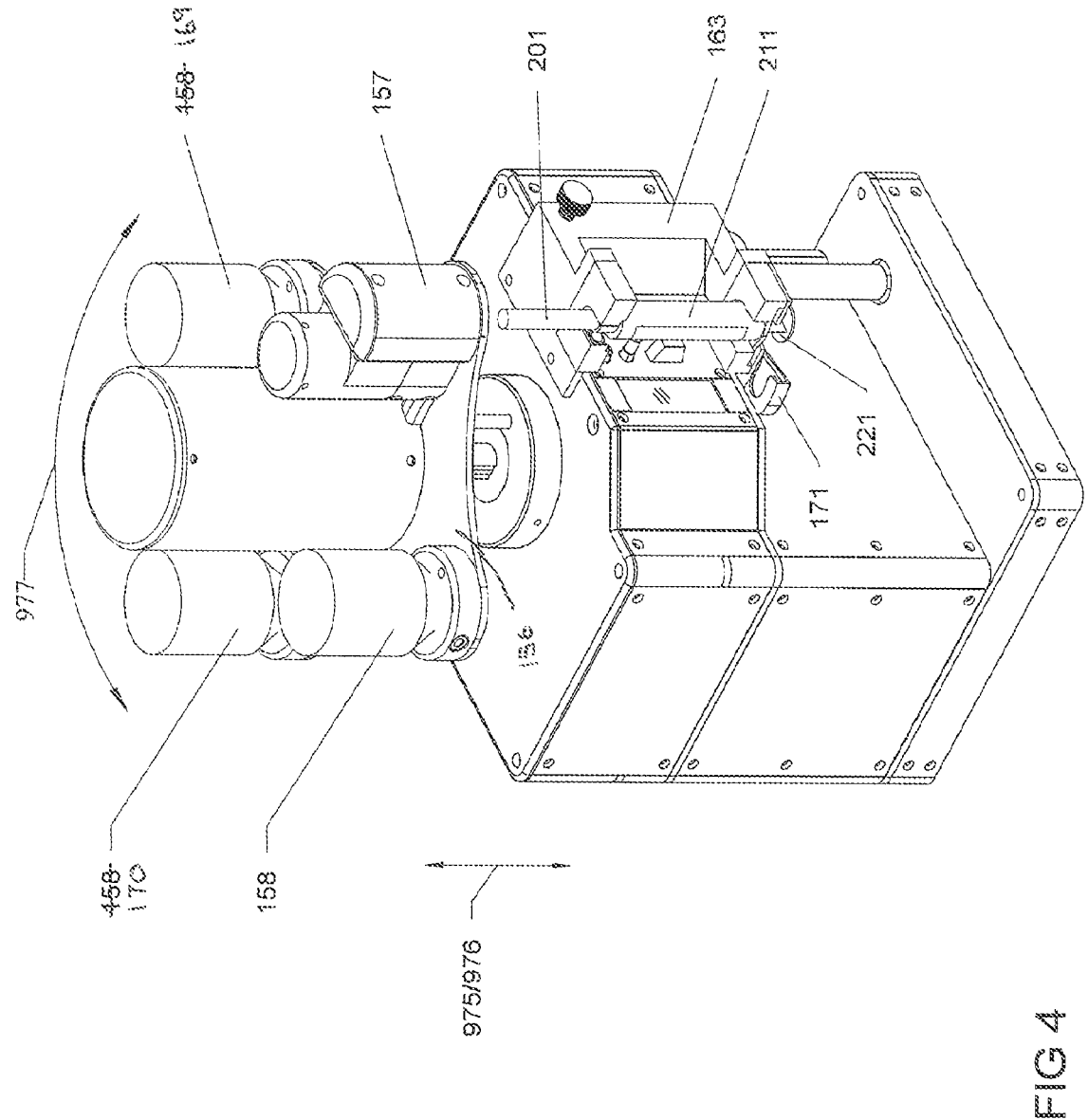
FIG. 4 illustrates the filler mechanism holding a capped syringe with the needle cap extractor positioned above the syringe needle cap. The optional single syringe holder is shown. Three inverted vials are also illustrated. The syringe plunger is shown compressed within the syringe.

Referencing FIG. 4, the disclosure also includes the ability of the top rotating plate 156 of the filler mechanism 149 to position the automated needle cap extractor 157 above a capped syringe 211 (with cap 201) positioned vertically in a slot of the carousel or in the illustrated optional single syringe holder 163. Further, the motor may rotate the top rotating plate to move the automated needle cap extractor from the position over the syringe and replace the extractor/installer with a vial of solution. In another embodiment, the vial may be empty and the contents of the syringe are added to the vial as discussed more thoroughly below. The horizontal direction of rotation of the rotating plate is shown by vector arrow 977. In one embodiment, the rotating plate rotates in one direction. In another embodiment, the rotating plate can rotate in both directions (clockwise and counter clockwise). In one embodiment, the vial 158 is inverted and the contents held by a septum. The septum surface is opposite the upward pointed needle. FIG. 4 illustrates three inverted vials 158, 169, 170.

Figure 10:
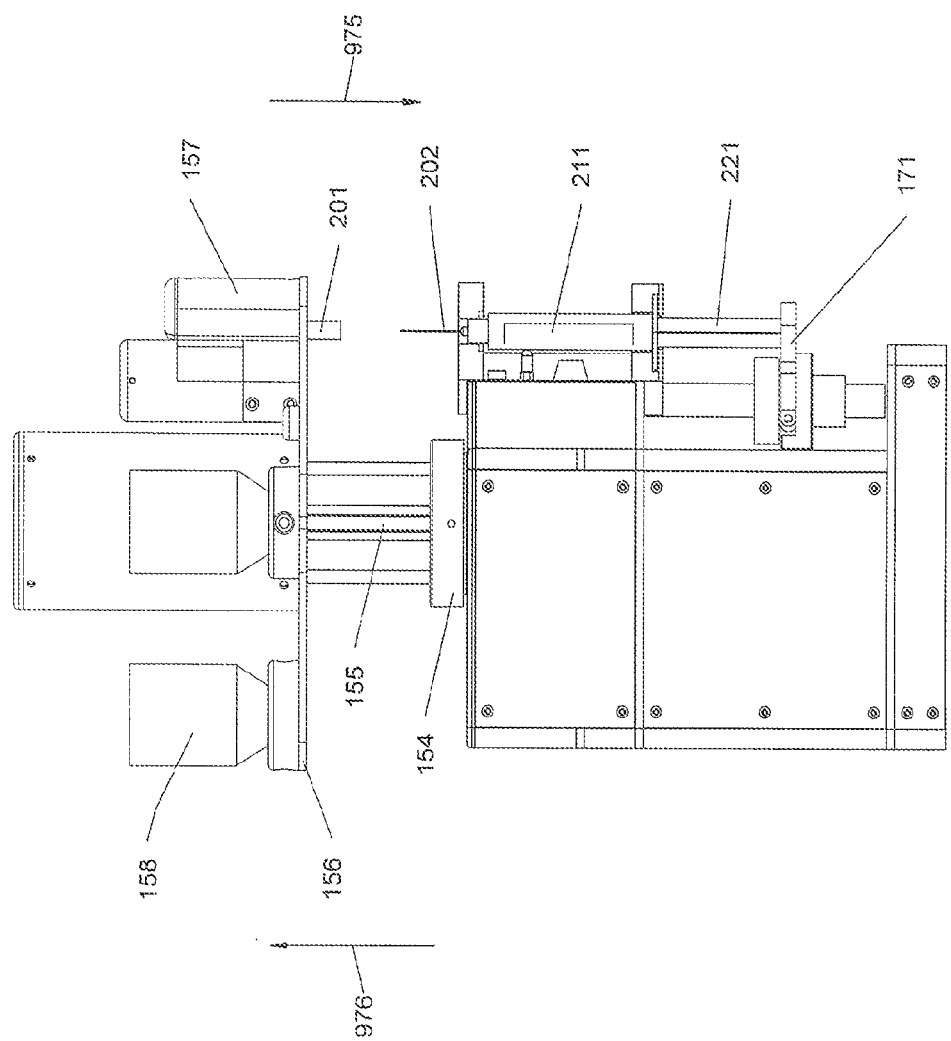
FIG. 10 illustrates the needle cap extractor (with the syringe cap) having rotated over the syringe needle.
Figure 17:
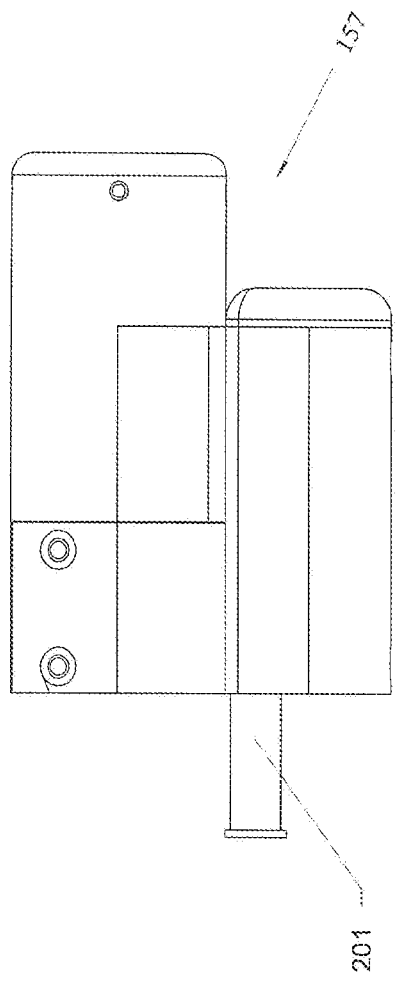
FIG. 17 is a side view of the needle cap extractor (with the syringe cap) with the exterior covers.
Figure 18:
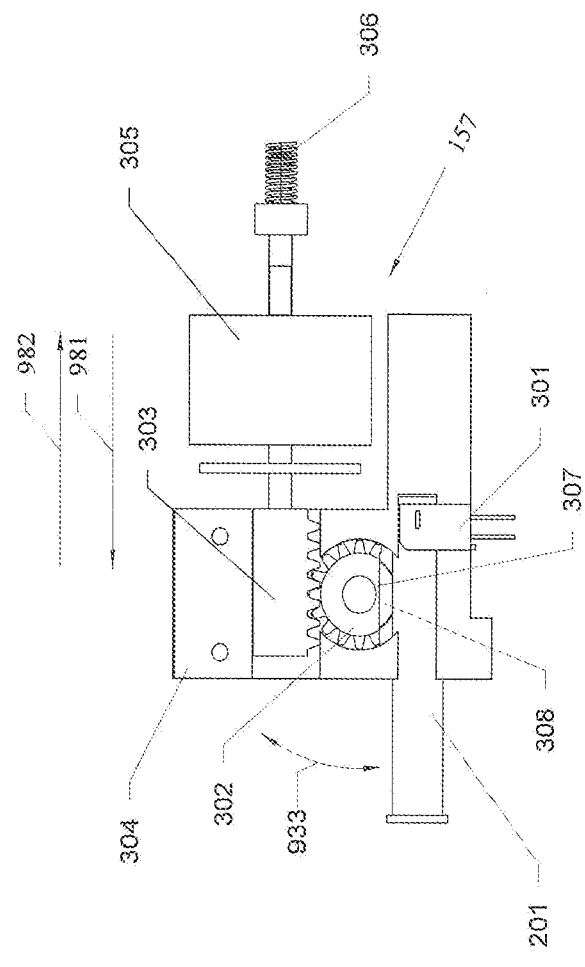
FIG. 18 is a side view of the needle cap extractor (with the syringe cap) without the exterior covers, illustrating the modified pinion and rack subcomponents for gripping the syringe cap and the direction of motion of the extractor and the rotating pinion.
Figure 19:
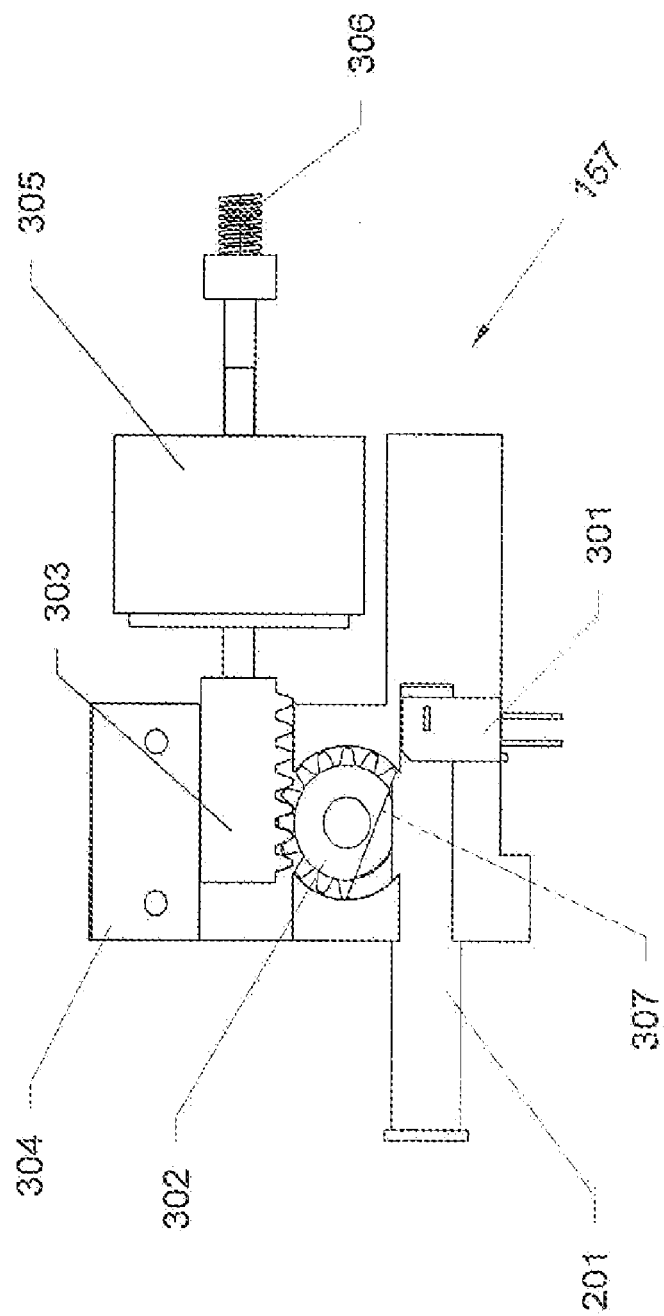
FIG. 19 is a side view of the needle cap extractor (with the syringe cap) without the exterior covers, showing movement of the rack rotating the pinion which grips the syringe cap.

FIG. 17 illustrates a detailed side view of the needle cap extractor 157. Illustrated are the covers covering the several subcomponents. FIG. 18 illustrates the subcomponents of the needle cap extractor 157. The subcomponent is in an access position, i.e., the modified pinion 302 is positioned so the flat surface 307 is directed to the cap holding space 308. Illustrated is a sensor 301 that detects the presence of a cap in the extracted or installation position. The sensor can be used to confirm the extraction or installation operation was successful. When a cap is detected, the solenoid actuator 305 can be signaled to move in an upward direction (vector arrow 982). This movement causes the modified pinion 307 to rotate (vector arrow 983) bringing the edge of the pinion into contact with the surface of the syringe cap 201. This contact 309 is shown in FIG. 19. This contact holds the cap in place when the needle cap extractor is elevated upward (vector arrow 976) as shown in FIG. 10. A spring 306 can be utilized to push the rack forward (vector arrow 981) to rotate the modified pinion whereby the flat (modified) edge 307 of the pinion faces the access space. In order to release the needle cap, a spring 306 can be utilized to push the rack forward (vector arrow 981) to rotate the modified pinion whereby the flat (modified) edge 307 faces the access space.

Figure 5:
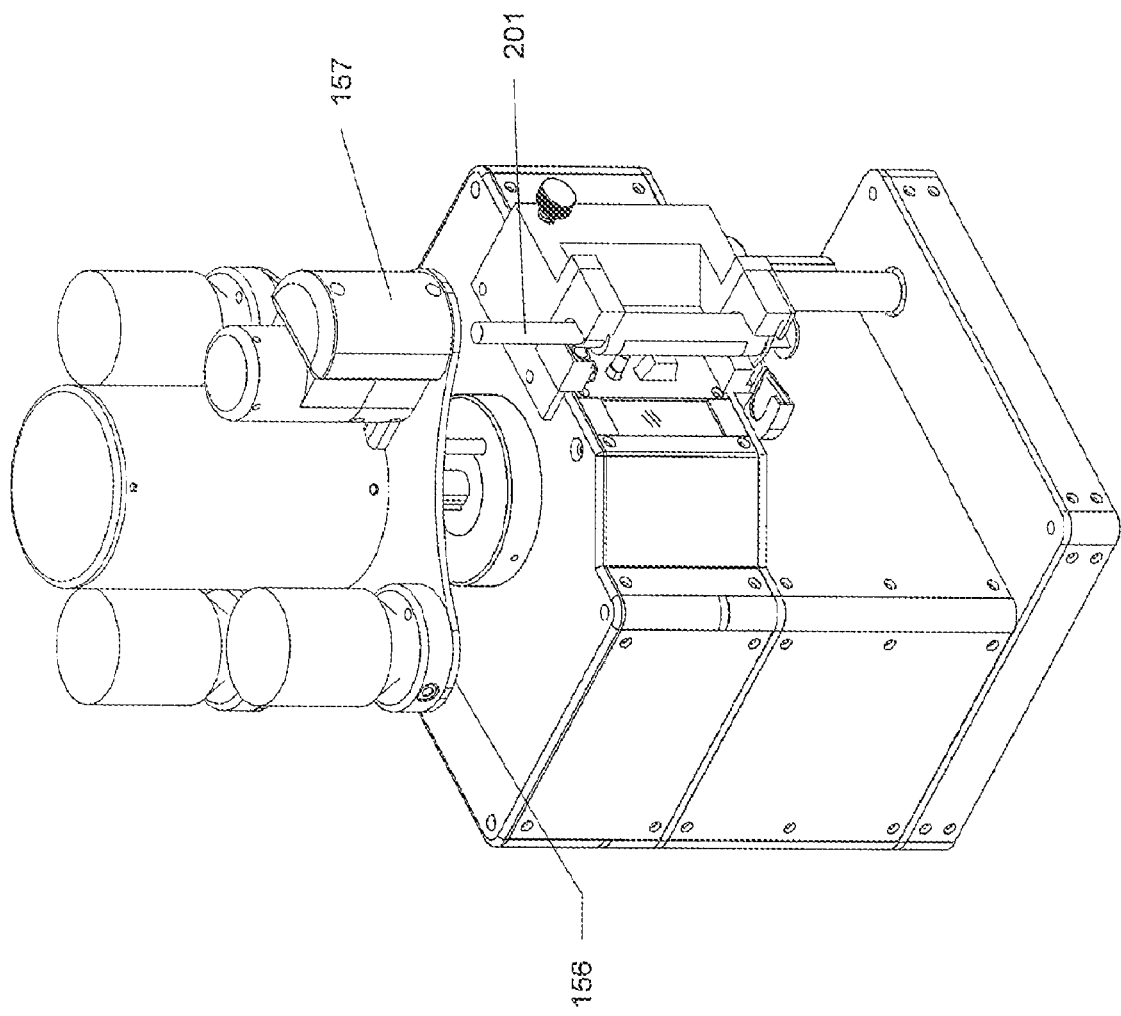
FIG. 5 illustrates a perspective view of the filler mechanism with the needle cap extractor positioned above the capped syringe needle.
Figure 6:
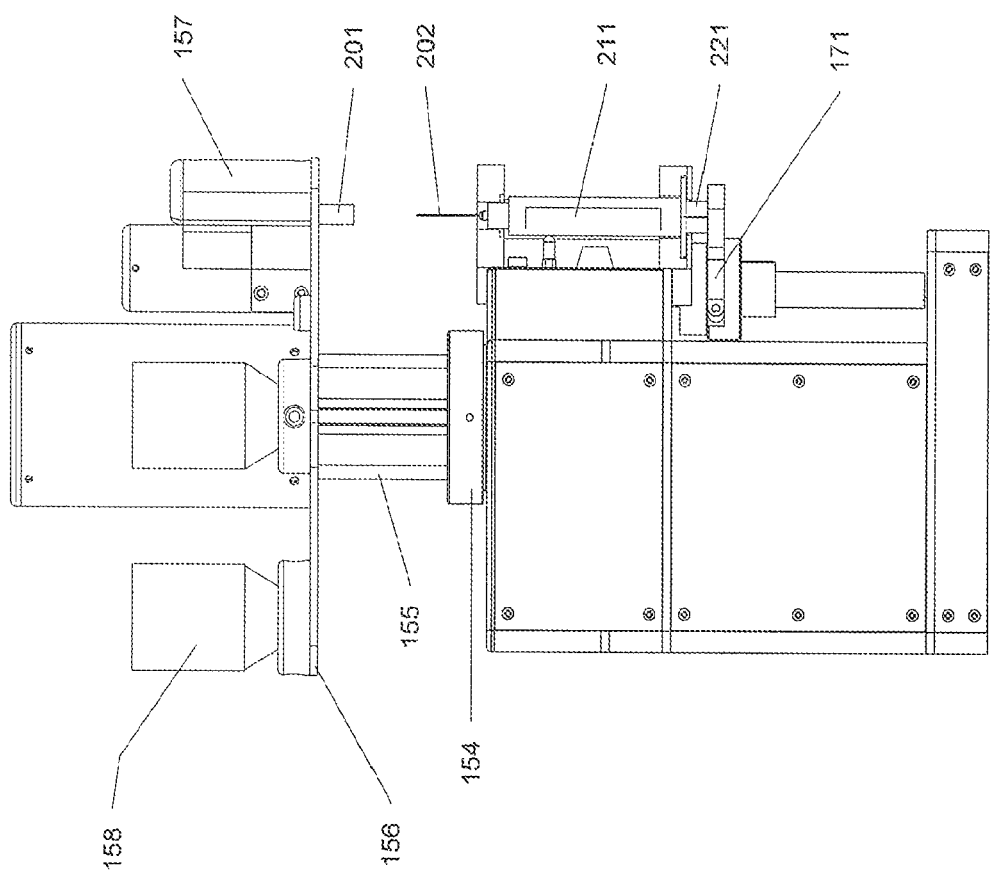
FIG. 6 illustrates a side view showing the syringe cap removed and the exposed syringe needle. The syringe plunger tool is in position to pull the syringe plunger downward.

The disclosure further includes the top rotating plate 156 having the capability to rotate 360 degrees and to move vertically up and down. The rotating plate 156 first rotates the automated needle cap extractor 157 above the syringe cap 201. See FIG. 5. The rotational movement is shown by vector arrow 977 in FIG. 13. FIG. 4 illustrates the up and down movement of the rotating plate with vector arrow 975/976. This up and down movement is used in the extraction of the syringe cap 201 from the syringe 211, thereby exposing the vertically oriented syringe needle 202. See FIGS. 5 and 6. The top rotating plate moves the automated needle cap extractor down over the syringe cap and the automated needle cap extractor 157 grasps the cap 201. The top rotating plate moves the automated needle cap extractor vertically upward (976 in FIG. 10) to expose the syringe needle 202. The operation of the automated needle cap extractor is driven by a solenoid. In another embodiment, one motor may be used to operate the cylindrical linear (vertical) movement actuator 155 and a second motor rotates the top rotating plate 156 on the axis of rotation. In one embodiment, the vertical motion is propelled by at least one vertical leg 155. There may be a central vertical leg that occupies the axis of rotation.

The syringe needle 202 is now exposed (cap removed). See FIG. 7. The inverted vial descends as shown by vector arrow 975 in FIG. 8. The vertical motion of the rotating plate 156 at the top of the filler mechanism can be used to control the descending motion. The vertically oriented needle pierces the septum of the vial 158. The open end of the needle 202 is now surrounded by solution. See FIG. 8. It will be appreciated that the rotating plate can hold one or more inverted vials. Illustrated in the Figures here is a rotating plate holding 3 inverted vials. Mounting more than 3 vials is possible and included within the scope of this invention.

Figure 9:
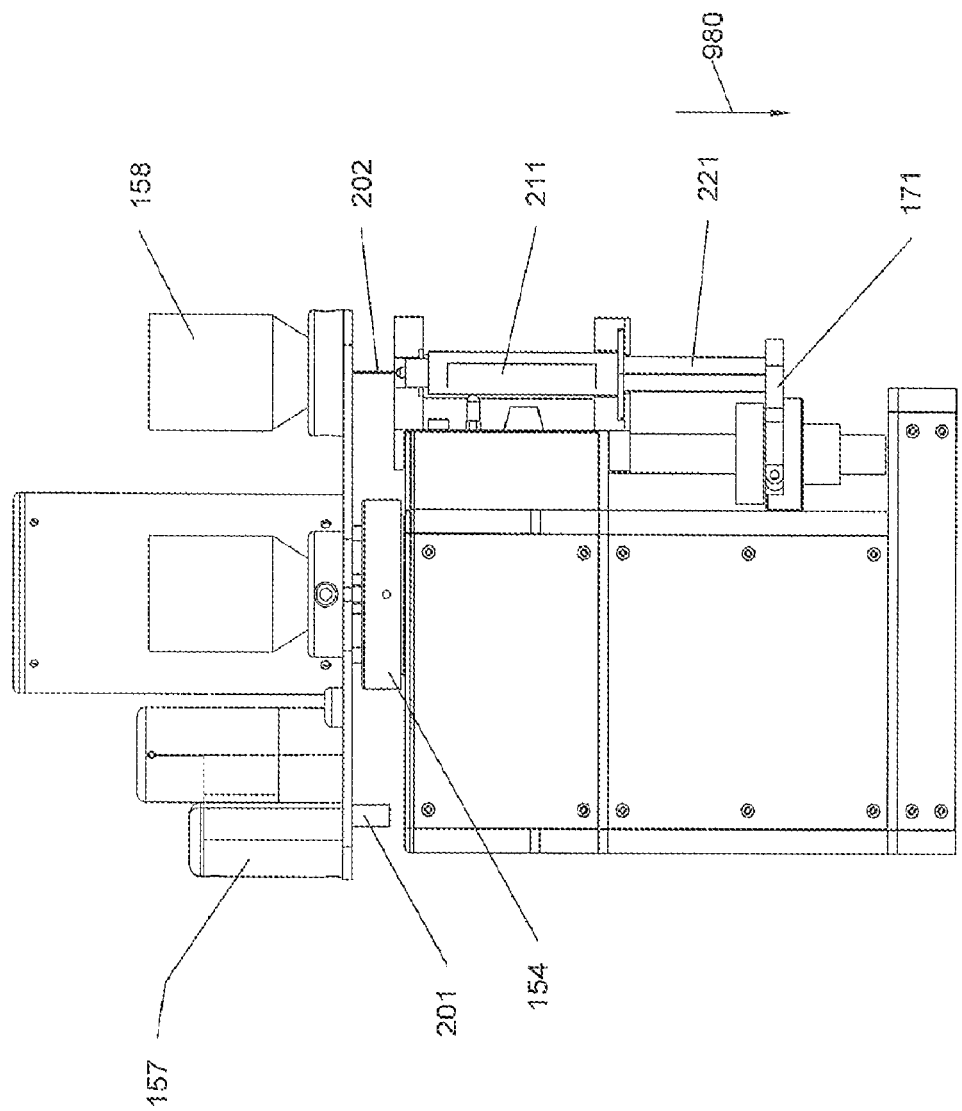
FIG. 9 is a side view showing the syringe plunger tool having moved downward pulling the syringe plunger down and causing the syringe to fill from the vial.

Recall that in one embodiment, the syringe plunger tool has engaged the syringe plunger. This can be the initial step of the fill sequence. The syringe plunger tool facilitates holding the vertically oriented syringe in a centered position when the automated needle cap extractor descends upon the cap. When engaged by suitable forward horizontal movement, the syringe plunger tool is then pushed downward (vertically) causing the syringe plunger to be pulled down a predetermined distance. This downward/vertical movement is shown by vector arrow 980 in FIG. 9. This causes a vacuum to be created in the body of the syringe 211 and the solution in the inverted vial 158 to be drawn down through the needle 202 into the syringe. The quantity of solution placed in the syringe can be controlled.

The syringe is now filled. The cap needs to be placed back on top of the syringe. See FIG. 10. The rotational plate 156 at the top of the dispenser mechanism is first elevated. This removes the needle from the septum. The rotatable plate is rotated to place the automated needle cap extractor 157 over the syringe needle 202. The motor then lowers the automated needle cap extractor containing the needle cap 201 over the needle. The cap extractor is lowered by the rotational plate 156 lowering as shown by vector arrow 975. The cap is released and reattached to the needle.

When the cap is reattached to the syringe 211, the syringe plunger tool 171 can be rotated back horizontally. (See item 171 and vector arrow 978 of FIG. 13.) The needle cap extractor can hold the syringe in place when the syringe plunger tool is rotated back horizontally. The syringe plunger tool can then be elevated by motor operation to its original position. See FIG. 4 illustrating the initial position of the syringe plunger tool.

Figure 11:
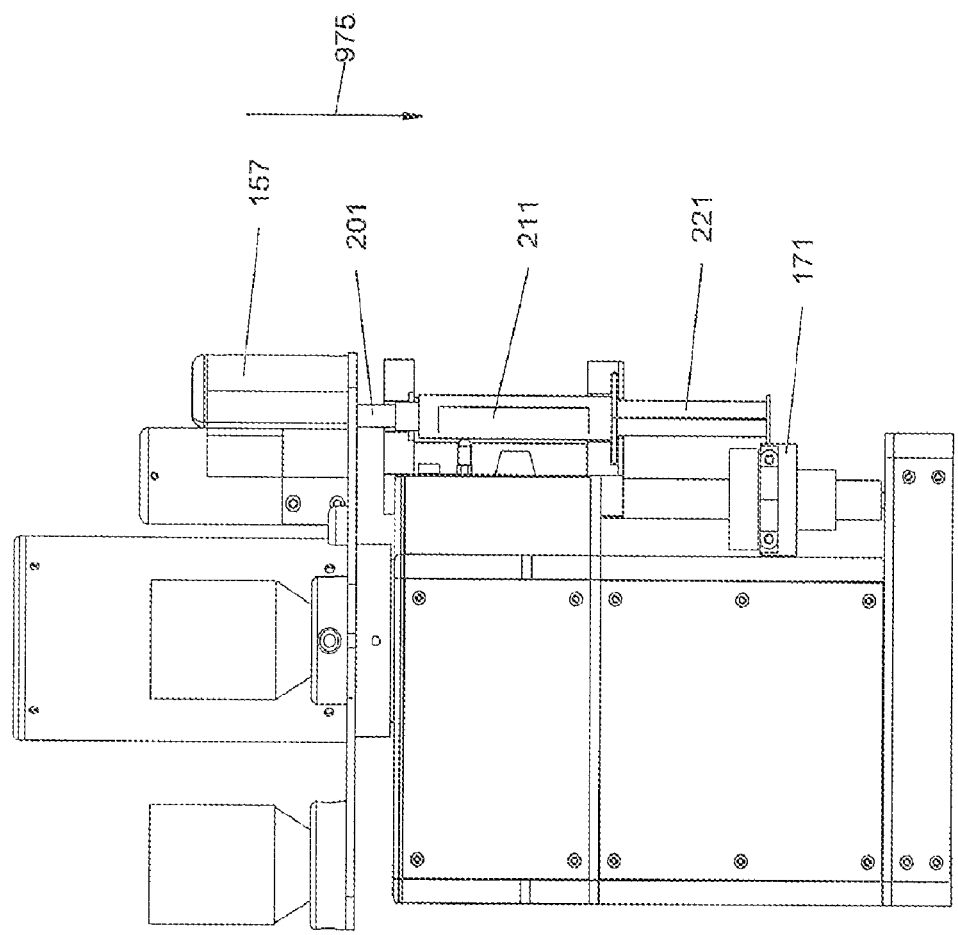
FIG. 11 is a side view illustrating the rotating plate containing the needle cap extractor descending upon the needle (replacing the syringe cap).
Figure 12:
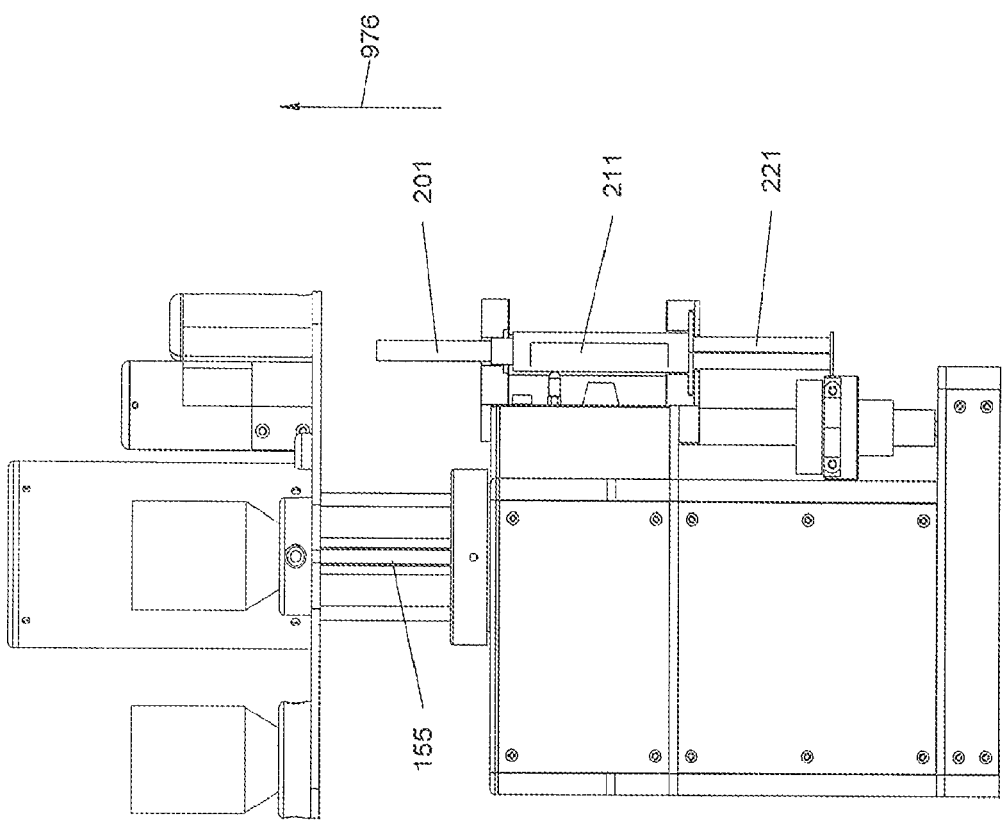
FIG. 12 is a side view showing the rotating plate and needle cap extractor elevating above the now capped and filled syringe.

The automated needle cap extractor is then elevated by the motor moving the rotational plate upward in the direction of vector arrow 976. See FIGS. 11 and 12.

The carousel can now rotate to bring an empty inverted syringe to the position beneath the automated needle cap extractor. The process is repeated of (i) engaging the syringe plunger tool with the syringe plunger (ii) cap removal, (iii) repositioning of the inverted vial, (iv) lowering of the vial onto the exposed needle, (v) moving the plunger down to fill the syringe with solution from the vial, (vi), elevating the inverted vial, (vii) repositioning the automated needle cap extractor, (viii) reattachment of the cap to the syringe, and (ix) disengagement of the syringe plunger tool. It will be appreciated the preceding sentence omits steps for brevity. These steps are described above or illustrated in the drawings.

Figure 13:
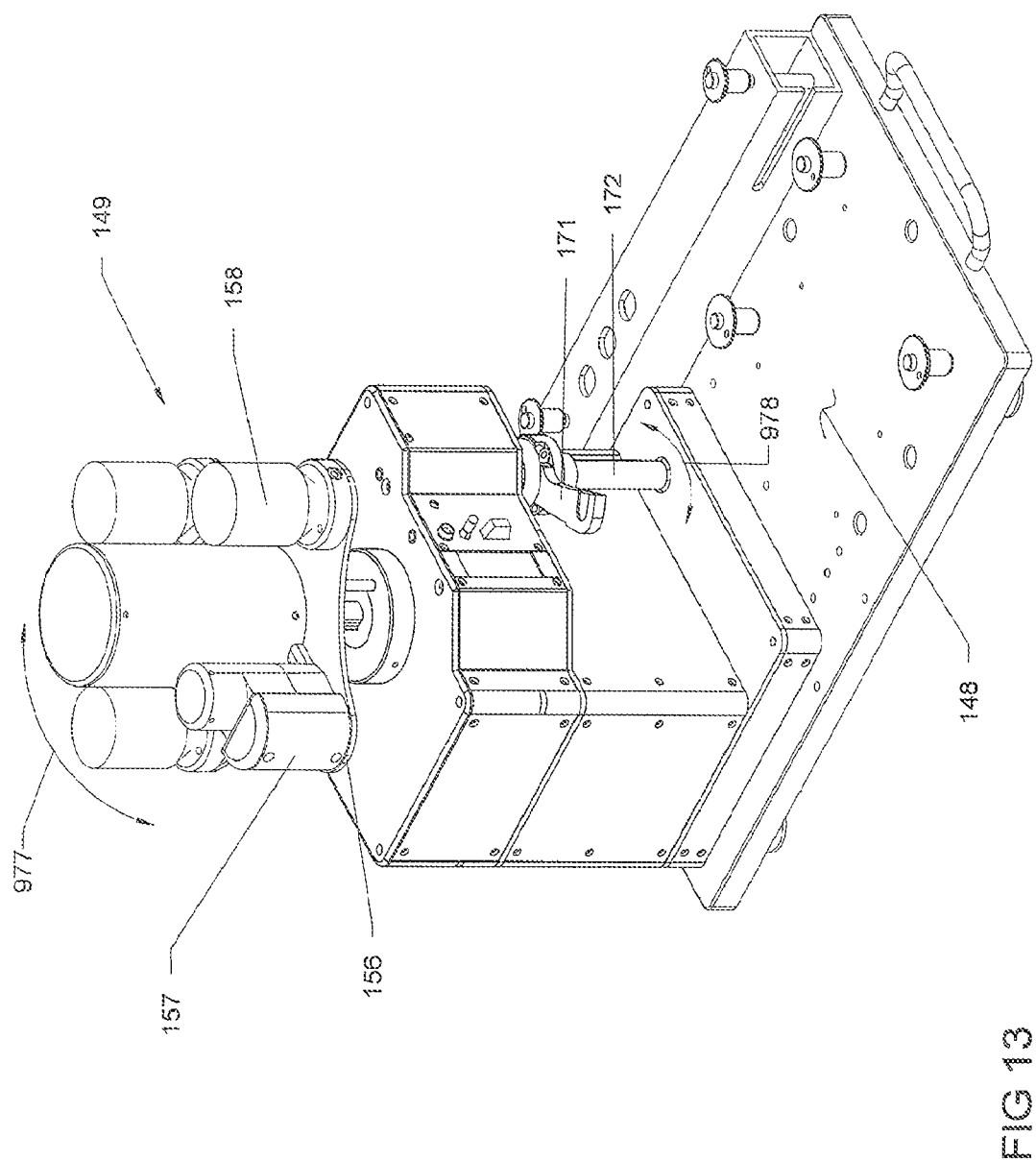
FIG. 13 is a perspective view of the rotating top of the filler mechanism showing three vials and the needle cap extractor. Also illustrated is the rotating syringe plunger tool.

FIG. 13 illustrates a perspective view of the filler mechanism 149. Also shown is the common base 148 upon which the rotating carousel actuator (not shown) can be mounted. The direction of rotation of the rotational plate 156 is also illustrated by vector arrow 977. The direction of rotation of the syringe plunger tool 171 is shown by vector arrow 978.

Figure 14:
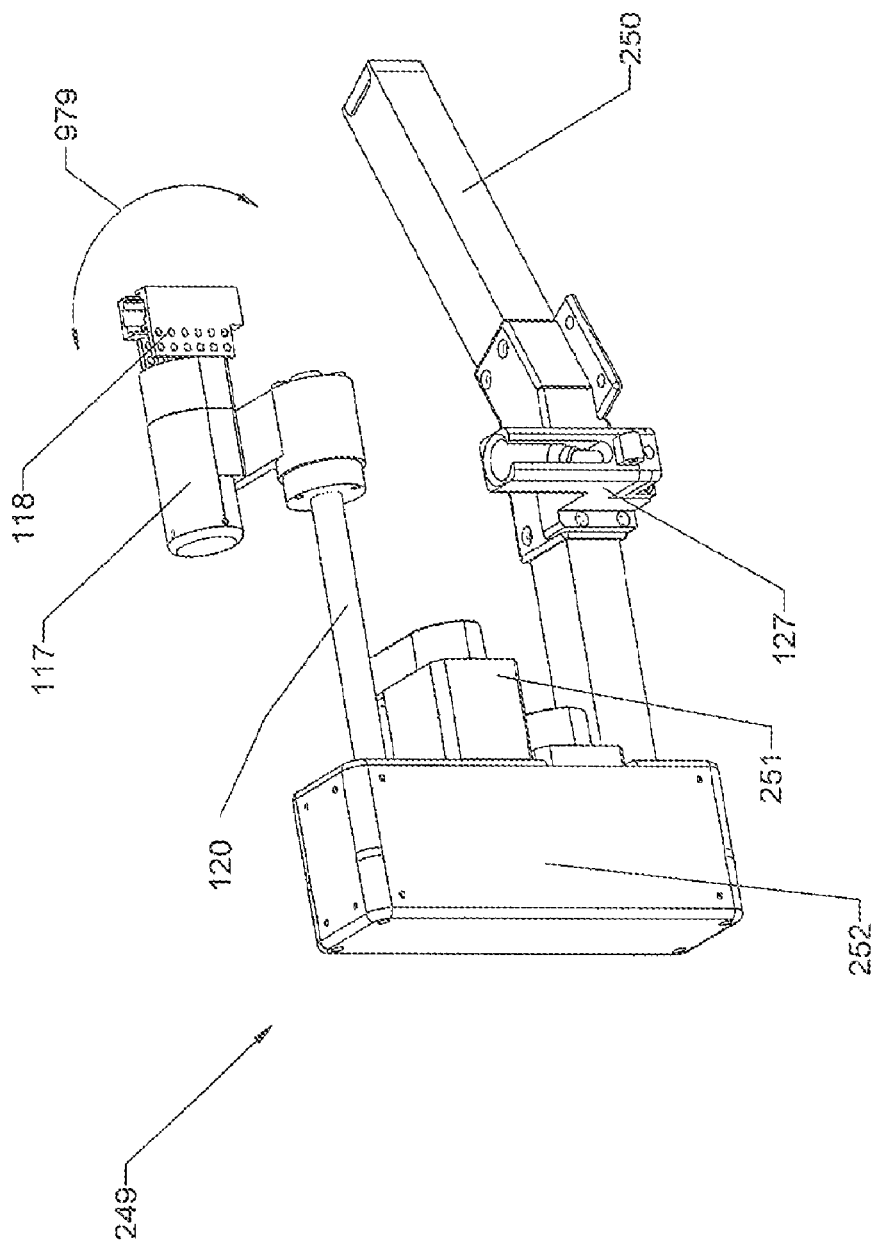
FIG. 14 is a perspective view of the automated syringe inverter component.

The next step performed by the apparatus is removing the filled syringe from the carousel and re-inverting the syringe so that the syringe cap is facing down. This task is accomplished by syringe inverter/extractor 249 illustrated in FIG. 14.

The carousel stops at a predetermined position in conjunction with the automated syringe inverter/extractor component. (This position of the carousel may simultaneously position another syringe, held by the carousel, directly beneath the automated cap extractor/installer. It will be appreciated that this positioning will allow two steps of the apparatus to occur simultaneously, i.e., filling of a syringe and extraction and inversion of a syringe from the carousel.)

Figure 15:
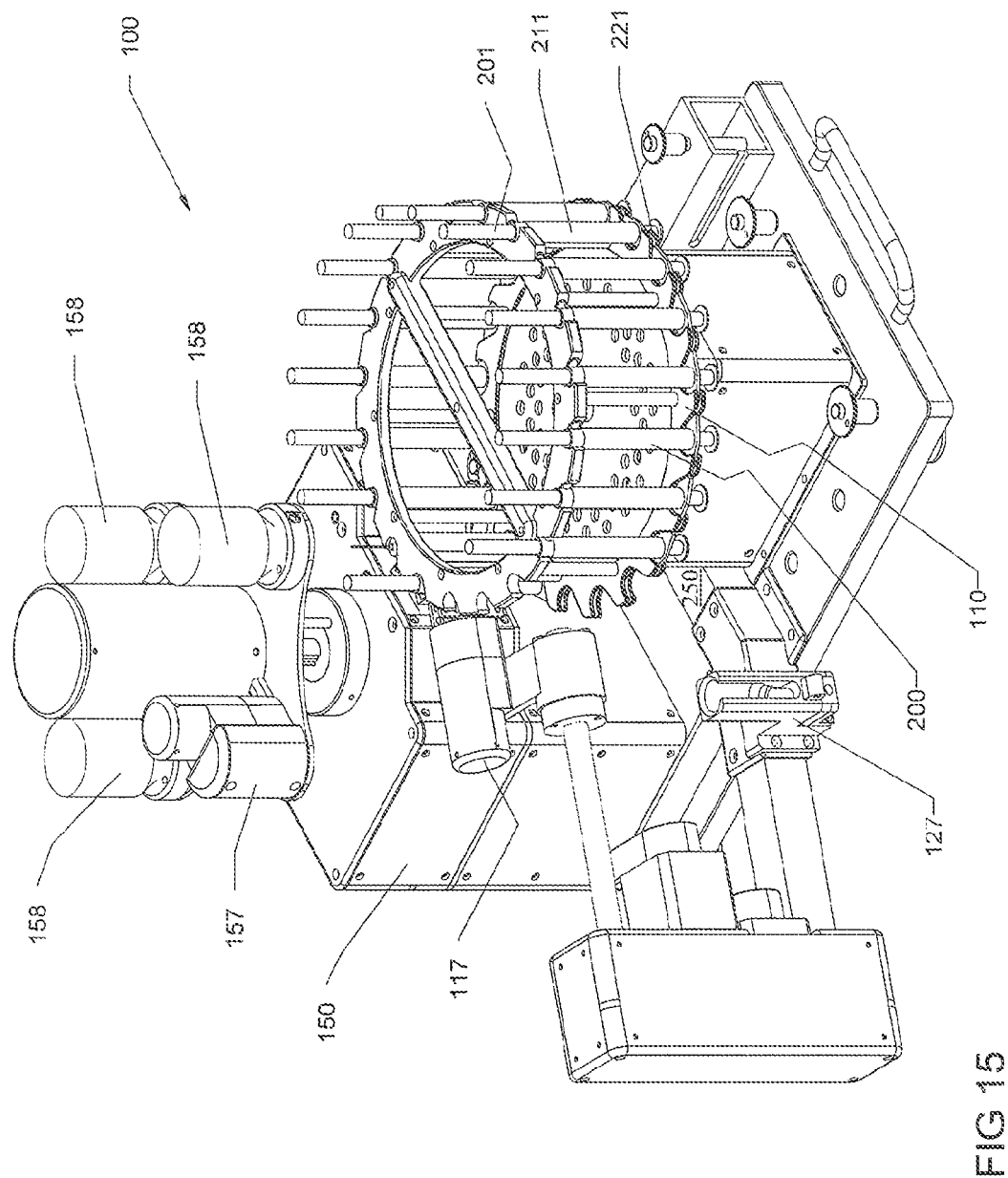
FIG. 15 is a perspective view of the three components subject of the disclosure, i.e., the rotating carousel, the filler mechanism and the automated syringe inverter component.
Figure 16:
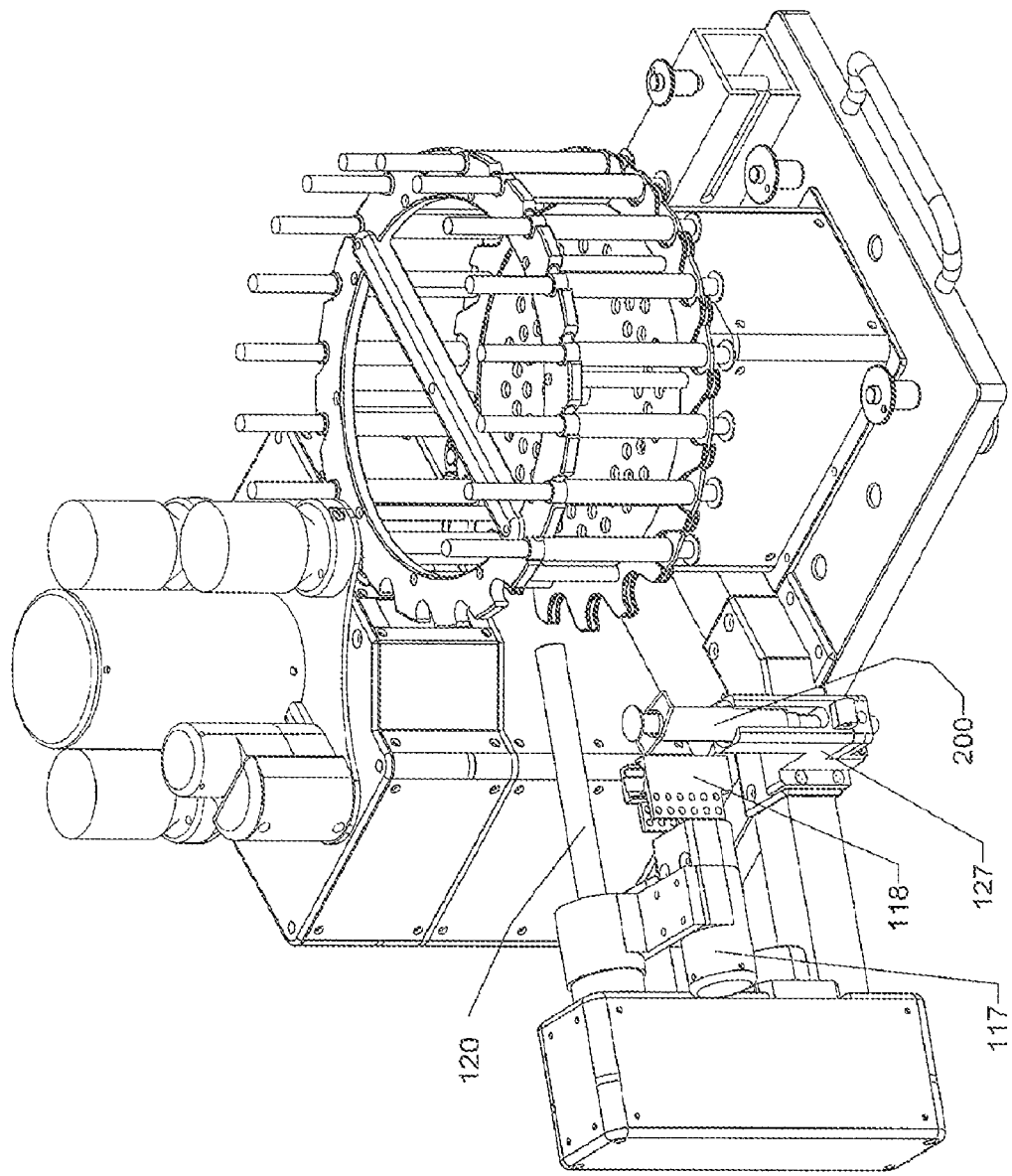
FIG. 16 is a perspective view of the automated syringe inverter component with an inverted syringe (cap side down) placed in a holder.

The syringe inverter/extractor can be attached to the dispenser mechanism or dispenser mechanism base by mount 250. See FIG. 15. This mechanism can ensure the correct distance relationship is maintained with the carousel. The component includes a motor 251 for rotational movement of a syringe gripper and a mechanism enclosure 252. The component also includes a second motor to move the syringe gripper forward and a gripper actuator to open and close the gripper jaws. The syringe gripper moves on a shaft/linear actuator 120. The gripper includes a gripper actuator 117. The gripper jaws 118 close on the syringe (not shown). The syringe is pulled horizontally out of the carousel. The syringe gripper component moves backward and forward on the shaft 120. At a predetermined distance the gripper actuator and jaws rotate 180 degrees on the shaft and place the syringe into a holder 127. It will be appreciated that the syringe cap will be in the down position in the holder. See syringe 200 in holder 127 in FIG. 16. The syringe may be removed from the holder either manually or through use of a separate automated device.

In another embodiment, the syringe inverter/extractor can be used to remove a filled syringe from the carousel and place the syringe in a shielded container thereby protecting the operator.

Figure 20:
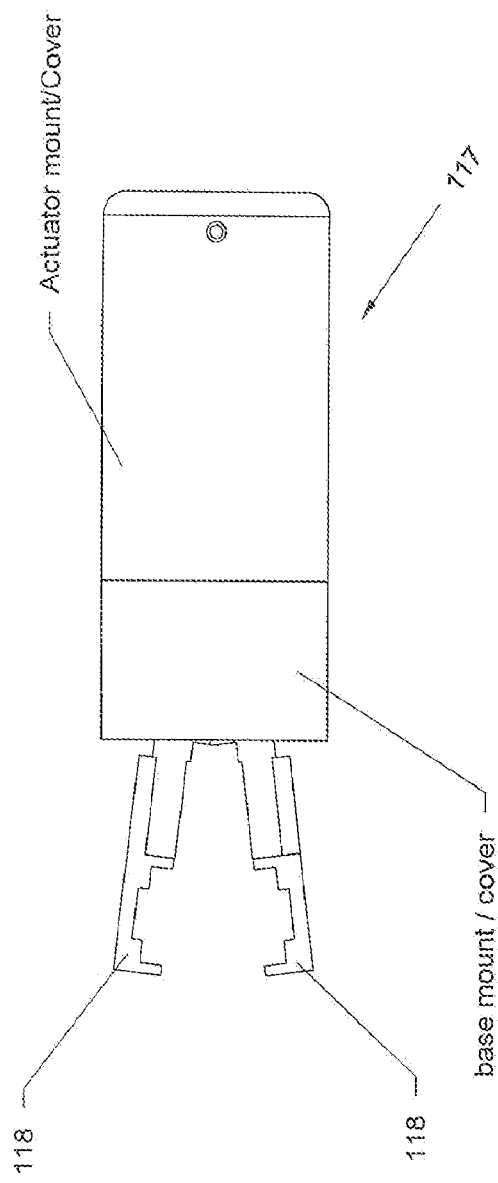
FIG. 20 is a top view of the gripper subcomponent and jaws of the automated syringe inverter component.
Figure 21:
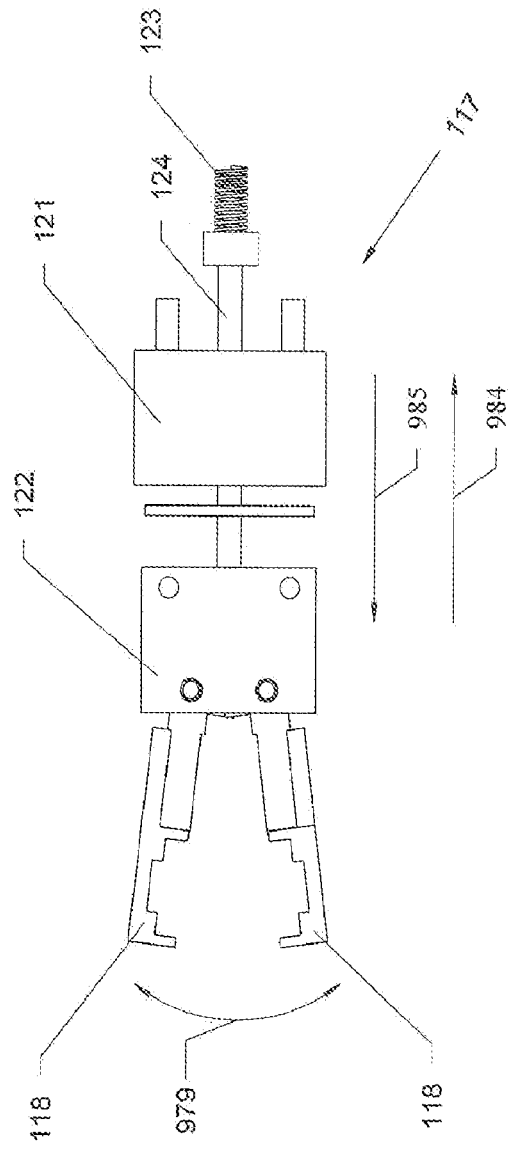
FIG. 21, a top view of the gripper subcomponent without the exterior covers, illustrates the direction of movement for opening and closing the gripper jaws and the direction of lateral movement of the gripper subcomponent.
Figure 22:
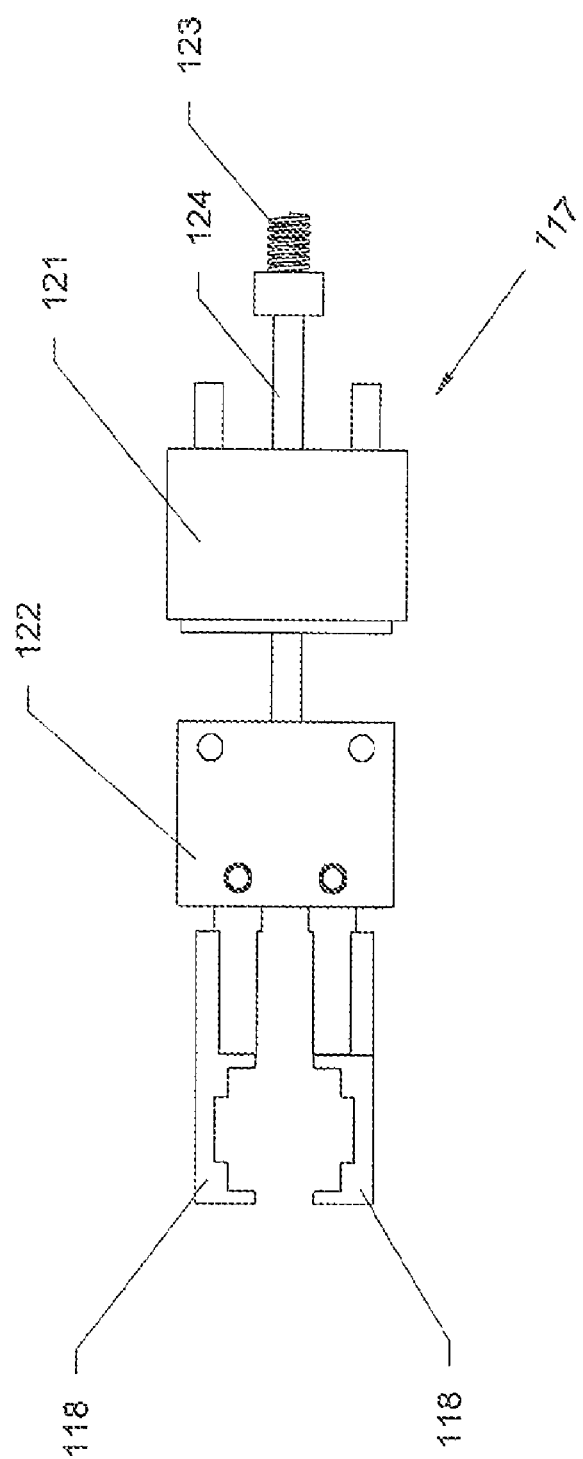
FIG. 22, a top view of the gripper subcomponent without the exterior covers, illustrates the gripper subcomponent with the gripper jaws in a closed position.

FIG. 20 illustrates a top view of the syringe gripper sub-component 117. Also illustrated are the gripper jaws 118. FIG. 21 illustrates the sub-component with the covers removed. Illustrated is the solenoid actuator 121 that moves the sub-component forward and backward on the shaft (not shown). The gripper body may contain hinge or pivoting sub-components in the gripper body 122 that cause the jaws 118 to pivot open and close. The hinge mechanism can be screw driven, a rack and pinion mechanism, or similar mechanism. The sub-component can include a spring 123 that pushes the actuator shaft 124 forward (vector arrow 985) to hold the jaws in an open position as the default position. The solenoid actuator may control the motion gripper in the reverse direction on the shaft (vector arrow 984).

It will also be appreciated that the apparatus may be configured to place the filled syringes into another rotating carousel for storage while the second carousel is filled without operator intervention. It will also be appreciated that the entire filing operation can be conducted in a shielded area. Other configurations with either the syringe cap up or down are within the scope of and included within this disclosure.

In another embodiment, the filled syringes can stay in the carousel and the entire carousel replaced by the operator with a replacement carousel of empty syringes.

In yet another embodiment, the syringes may be partially filled with solution when placed in the carousel and filled with additional solution by the filler mechanism.

The filler mechanism 149 can also be used to add solution to one or more vials from syringes containing solution. This process is basically the reverse of the syringe filling sequence. The syringe plunger tool is engaged with the syringe plunger. The syringe cap is removed by the automated needle cap extractor 157. The vertical motion of the rotating plate 156 at the top of the filler mechanism can also be used to lift the needle cap extractor. The rotating plate 156 can then horizontally rotate an inverted vial above the now exposed syringe needle. The vial can be lowered onto the needle. The syringe plunger tool can be elevated vertically, thereby pushing the syringe plunger upward. The solution within the syringe is discharged into the vial.

The filler mechanism can also be used to mix solutions within a vial. See FIG. 7. An empty syringe can be filled with a predetermined quantity of a first solution from a first vial 158 using the procedure described previously. The first vial can be lifted from the syringe needle 202. The rotating plate can rotate a second vial 169 above the exposed syringe needle. The second vial containing a second solution can be lowered onto the syringe needle. The syringe plunger tool 171 can be elevated, thereby pushing the syringe plunger upward and discharging the solution into the second vial. The quantity of solution in the second vial can also be predetermined.

In addition, this specification is to be construed as illustrative only and is for the purpose of teaching those skilled in the art the manner of carrying out the invention. It is to be understood that the forms of the invention herein shown and described are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention maybe utilized independently of the use of other features, all as would be apparent to one skilled in the art after having the benefit of this description of the invention.

While specific embodiments have been illustrated and described, numerous modifications are possible without departing from the spirit of the invention, and the scope of protection is only limited by the scope of the accompanying claims.

The invention claimed is:

1. An automated method for the filling of syringes comprising:
    a) a motor controlled rotatable carousel in a horizontal plane holding vertically one or more syringes wherein a cap of the syringe is on top and a syringe plunger is on the bottom;
    b) locating a motor controlled filler mechanism proximate to the rotatable carousel;
    c) a syringe plunger tool rotating from a first position of the motor controlled filler mechanism and engaging the syringe plunger held in the carousel at a second position;
    d) an automated needle cap extractor mounted on a motor controlled rotatable plate descending from a third position to a fourth position and grasping a syringe cap and removing the syringe cap by returning to the third position;
    e) the rotatable plate rotating horizontally to a fifth position wherein a perforatable surface of an inverted vial is positioned above an uncapped syringe needle;
    f) the inverted vial descending to a sixth position upon the needle;
    g) the syringe plunger tool pulling the syringe plunger downward a controlled distance to a seventh position;
    h) the inverted vial moving upward from the sixth position and returning to the fifth position causing the syringe needle to be extracted from the inverted vial;
    i) the rotatable plate rotating the automated needle cap extractor horizontally and stopping at the third position with the cap component directly above the needle;
    j) the automated needle cap extractor descending to the fourth position upon the needle to replace the needle cap; and
    k) the syringe plunger tool disengaging from the syringe plunger and returning to the fifth position and the automated needle cap extractor returning to the third position.

2. The method of claim 1 further comprising the steps:
    a) the motor controlled carousel rotating to a seventh position proximate to a motor controlled syringe inverter wherein a gripping jaw subcomponent of the syringe inverter moves from a eighth position to a ninth position and grasps the syringe and retracts to the eighth position whereby the syringe is removed from the carousel;
    b) the syringe inverter holding the syringe with the syringe cap at the top rotates in a vertical plane to a tenth position wherein the syringe cap is at the bottom and the gripping jaw sub-component is released.

3. The method of claim 1 further comprising reading a barcode on the syringe.

4. The method of claim 1 further comprising reading a barcode on a vial.

5. An automated apparatus for the filling of syringes comprising:
    a) a motor controlled removable rotatable carousel in a horizontal plane and capable of holding vertically one or more capped syringes wherein a capped syringe is on top and a syringe plunger is on the bottom; and
    b) a motor controlled filler mechanism located proximate to the rotatable carousel and comprising a syringe plunger tool that is rotatable and can be raised and lowered, and a rotatable plate that can be raised and lowered and capable of holding at least one inverted vial and an automated needle cap extractor.

6. The apparatus of claim 5 wherein the automated cap extractor/installer comprises a rack and modified pinion.

7. The apparatus of claim 5 further comprising a motor controlled syringe inverter/extractor comprising a gripping jaw subcomponent that can be moved forward and back and rotated.

8. The apparatus of claim 5 further comprising a barcode reader.

9. The apparatus of claim 8 wherein the barcode reader is mounted on the filler mechanism.

10. The apparatus of claim 5 wherein the inverted vial contains radiopharmaceuticals.

11. The apparatus of claim 6 wherein the rotatable plate is capable of holding up to three inverted vials.

12. The apparatus of claim 6 wherein at least one motor control is a step motor.

13. The apparatus of claim 6 wherein at least one motor is a servo motor.

14. The apparatus of claim 6 wherein the rotatable plate is capable of holding up to five inverted vials.

15. The apparatus of claim 6 wherein the rotatable plate is capable of holding up to six inverted vials.

* * * * *